US010820808B2

United States Patent
(12) United States Patent
Barodka

(10) Patent No.: US 10,820,808 B2
(45) Date of Patent: Nov. 3, 2020

(54) DEVICE AND METHOD TO MEASURE VENTRICULAR ARTERIAL COUPLING AND VASCULAR PERFORMANCE

(71) Applicant: THE JOHNS HOPKINS UNIVERSITY, Baltimore, MD (US)

(72) Inventor: Viachaslau Barodka, Baltimore, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 799 days.

(21) Appl. No.: 15/449,410

(22) Filed: Mar. 3, 2017

(65) Prior Publication Data

US 2017/0251929 A1 Sep. 7, 2017

Related U.S. Application Data

(60) Provisional application No. 62/302,884, filed on Mar. 3, 2016.

(51) Int. Cl.
*A61B 5/0205* (2006.01)
*A61B 5/0452* (2006.01)
(Continued)

(52) U.S. Cl.
CPC ........ *A61B 5/02028* (2013.01); *A61B 5/0205* (2013.01); *A61B 5/02007* (2013.01);
(Continued)

(58) Field of Classification Search
CPC ... A61B 5/0205; A61B 5/0432; A61B 5/0022; A61B 5/02416; A61B 5/0402;
(Continued)

(56) References Cited

U.S. PATENT DOCUMENTS 8,428,720 B2 * 4/2013 Corbucci ........... A61B 5/02028 607/19
2003/0109772 A1 6/2003 Mills
(Continued)

OTHER PUBLICATIONS

Salvi et al., Left ventricular ejection time, not heart rate, is an independent correlate of aortic pulse wave velocity, J Appl Physiol 115 : 1610-1617, 2013. First published Sep. 19, 2013; doi:10.1152/japplphysiol.00475.2013.*
(Continued)

*Primary Examiner* — John R Downey
(74) *Attorney, Agent, or Firm* — MH2 Technology Law Group LLP

(57) ABSTRACT

A device and method for analyzing of a disturbed pattern of pulse wave front results in a non-invasive, real-time diagnostic tool of arterial vascular performance on both a global and regional scale. The device provides a single number quantifying how well the arterial tree as a whole is coupled to receive and distribute a stroke volume of a single heartbeat. Changing heart rate, contractility, volume status, and afterload will change stroke volume and ejection time. Different vasculatures with different properties (e.g., size and intrinsic stiffness) will be best matched for different stroke volumes and ejection times to provide optimal coupling. The device will allow finding the optimal set of parameters for individual patient.

19 Claims, 4 Drawing Sheets

(51) Int. Cl.

| | |
|---|---|
| ***A61B 5/00*** | (2006.01) |
| ***A61B 5/029*** | (2006.01) |
| ***A61B 5/02*** | (2006.01) |
| ***A61B 5/026*** | (2006.01) |
| ***A61B 5/0456*** | (2006.01) |
| ***A61B 5/021*** | (2006.01) |
| ***A61B 7/00*** | (2006.01) |
| *A61B 7/04* | (2006.01) |
| *A61B 5/024* | (2006.01) |
| *A61B 5/08* | (2006.01) |

(52) U.S. Cl.

CPC .......... *A61B 5/029* (2013.01); *A61B 5/02125* (2013.01); *A61B 5/0452* (2013.01); *A61B 5/6824* (2013.01); *A61B 5/6826* (2013.01); *A61B 5/6828* (2013.01); *A61B 5/6829* (2013.01); *A61B 7/00* (2013.01); *A61B 5/021* (2013.01); *A61B 5/026* (2013.01); *A61B 5/02416* (2013.01); *A61B 5/0456* (2013.01); *A61B 5/082* (2013.01); *A61B 5/742* (2013.01); *A61B 7/04* (2013.01); *A61B 2562/04* (2013.01)

(58) Field of Classification Search

CPC ..... A61B 5/046; A61B 5/0464; A61B 5/7275; A61B 5/721; A61B 5/024; A61B 5/02077; A61B 5/02108; A61B 5/02125; A61B 5/029; A61B 5/6814; A61B 5/6815; A61B 5/6824; A61B 5/6825; A61B 5/6826; A61B 5/6828; A61B 5/6829

USPC ................ 600/301, 324, 483, 500, 509, 513

See application file for complete search history.

(56) References Cited

U.S. PATENT DOCUMENTS

2003/0163058 A1 8/2003 Osypka et al.
2004/0015091 A1* 1/2004 Greenwald ........ A61B 5/02125 600/513
2004/0077934 A1 4/2004 Massad
2007/0027369 A1* 2/2007 Pagnacco ............. A61B 5/1071 600/301
2008/0139953 A1* 6/2008 Baker .................. A61B 5/0006 600/509
2008/0221930 A1* 9/2008 Wekell ............... A61B 5/02055 705/3
2010/0049069 A1* 2/2010 Tarassenko .......... A61B 5/0452 600/512
2010/0185068 A1* 7/2010 Park ....................... A61B 5/021 600/324
2011/0009712 A1* 1/2011 Fayram ................ A61B 5/0084 600/301
2011/0009754 A1* 1/2011 Wenzel ................ A61B 5/0215 600/485
2012/0108915 A1* 5/2012 Corbucci ........... A61B 5/02028 600/301
2012/0143067 A1* 6/2012 Watson .............. A61B 5/02108 600/485
2013/0090566 A1* 4/2013 Muhlsteff .......... A61B 5/02028 600/500
2015/0018631 A1* 1/2015 Lee ...................... A61B 5/7282 600/301
2016/0073911 A1* 3/2016 Hallab ............... A61B 5/02125 600/479
2016/0345845 A1* 12/2016 Ravid .................. A61B 5/0285
2017/0079533 A1* 3/2017 Robinson ........... A61B 5/02007
2017/0156706 A1* 6/2017 Joseph .................... G06F 19/00
2017/0238818 A1 8/2017 Gaurav et al.
2017/0340228 A1* 11/2017 Dirkes ................ A61B 5/0404
2018/0085011 A1* 3/2018 Ma ....................... A61B 5/7235
2018/0235567 A1 8/2018 Bezemer et al.
2018/0360325 A1* 12/2018 Robinson ........... A61B 5/02125

OTHER PUBLICATIONS

Minke C Kortekaas et al 2012 Physiol. Meas. 33 1993 (Year: 1993).*
Desaive et al., Assessment of ventricular contractility and ventricular-arterial coupling with a model-based sensor. (2013) Computer Methods and Programs in Biomedicine, 109(2), pp. 182-189.

* cited by examiner

DEVICE AND METHOD TO MEASURE VENTRICULAR ARTERIAL COUPLING AND VASCULAR PERFORMANCE

CROSS-REFERENCE TO RELATED APPLICATIONS

The present application claims priority to U.S. Provisional Patent Application No. 62/302,884, filed on Mar. 3, 2016, which is hereby incorporated by reference in its entirety.

FIELD OF THE INVENTION

The present invention relates generally to hospital management. More particularly, the present invention relates to emergency room management software to support an objective triage evaluation.

BACKGROUND OF THE INVENTION

When the heart contracts, it sends a bolus of blood, the stroke volume, into the arterial vascular system, which then distributes the blood to the peripheral tissue. The time taken for a pulse wave to arrive from the heart to peripheral tissue depends on the distance travelled and velocity of the pulse wave, which is determined by various arterial physical properties such as vessel diameter, wall thickness, and compliance. Pulse wave velocity (PWV) has been extensively studied. However, the pattern of pulse arrival into different peripheral vascular beds is not well studied.

Therefore, it would be advantageous to provide a device and method to measure ventricular arterial coupling and vascular performance using timing of the pulse arrival into different peripheral vascular beds.

SUMMARY OF THE INVENTION

The foregoing needs are met, to a great extent, by the present invention, wherein in one aspect, a device for measuring a pulse wave front includes sensors for measuring metrics related to arterial reception and distribution of stroke volume of a heartbeat. The device also includes a non-transitory computer readable medium. The non-transitory computer readable medium is programmed for receiving data from the sensors and processing the data to determine the function of an arterial tree. The non-transitory computer readable medium is also programmed for generating a metric related to reception and distribution of the pulse stroke volume by the arterial tree.

In accordance with an aspect of the present invention, the device includes the sensors. The sensors include an electrocardiograph (EKG) and any sensor which is able to detect pulse arrival (e.g., pulse plethysmograph (PPG), pulse oximetry or continuous BP waveform detection (such as applanation tonometer or finapress). The pulse arrival sensors are configured for the ear, finger, and toe. The device is configured for simultaneously recording from the EKG and the pulse arrival sensors. The device is also programmed for determining the arrival of the pulse stroke volume recorded at the ear, the finger, and/or the toe.

In accordance with another aspect of the present invention, a method for measuring a pulse wave front includes receiving data from sensors for measuring metrics related to arterial reception and distribution of a pulse stroke volume and processing the data to determine a function of an arterial tree. The method also includes generating a metric related to reception and distribution of the pulse stroke volume by the arterial tree.

In accordance with still another aspect of the present invention, the method includes executing the steps of the method with a non-transitory computer readable medium. The method includes measuring the arrival of a pulse stroke volume at one selected from a group consisting of an ear, a toe, and a finger. The method includes simultaneously recording from a pulse plethysmograph and an electrocardiogram. The method includes generating a visual display of the reception and distribution of the pulse stroke volume by the arterial tree.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

Figure 1:
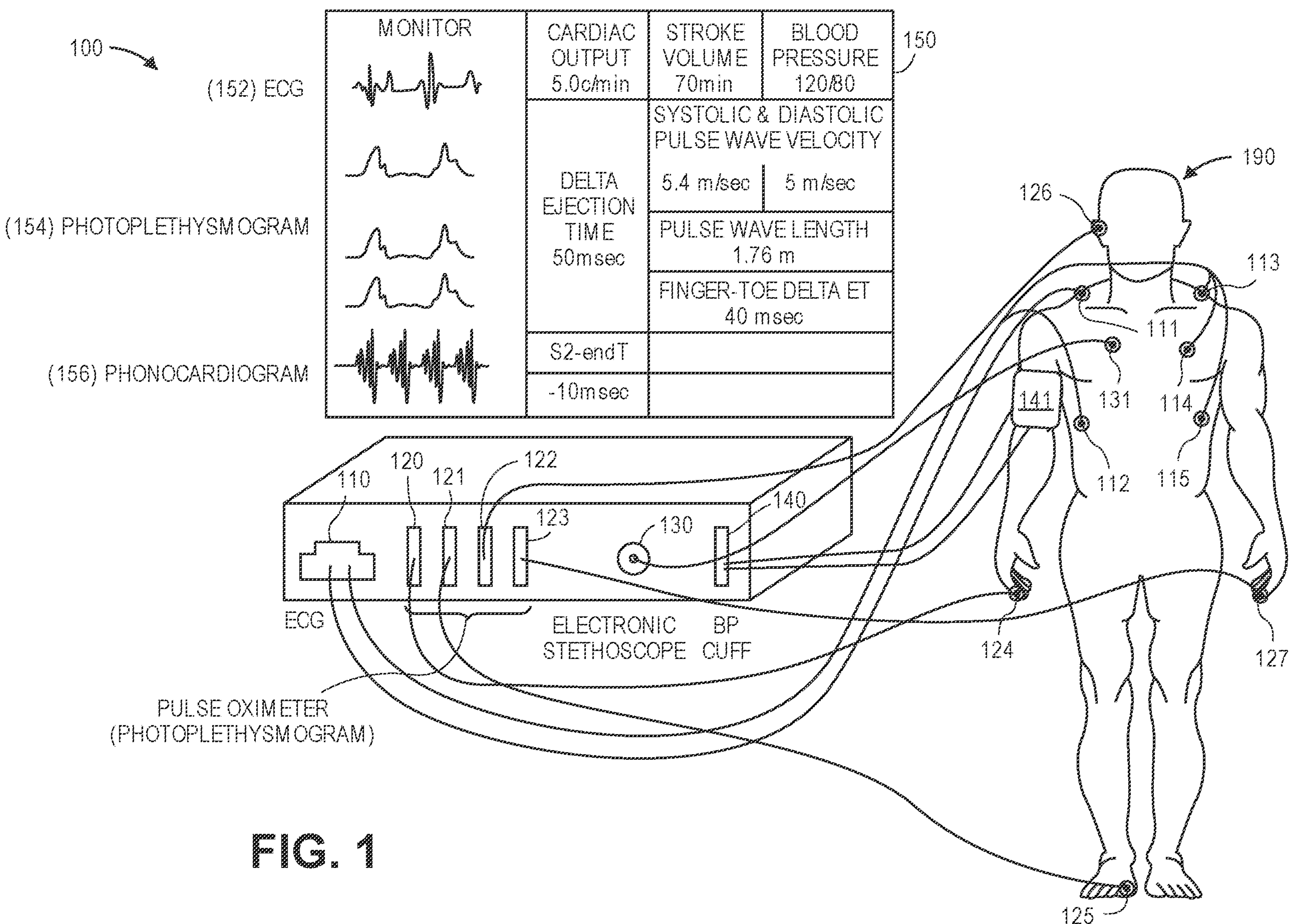
FIG. 1 illustrates a device for measuring an arterial vascular performance of a subject.

FIG. 1 illustrates a device 100 for measuring an arterial vascular performance of a subject 190. The device 100 may include one or more EKG inputs (one is shown: 110). The EKG input 110 may be configured to receive signals from one or more sensors (five are shown: 111-115) that are coupled to the subject 190. As shown, the sensors 111-115 may be coupled to the subject's chest, shoulders, torso, and/or back. The signals may be or include EKG signals (e.g., Q, R, S, T waves).

The device 100 may also include two or more pulse oximeter inputs (four are shown: 120-123). The pulse oximeter inputs 120-123 may be configured to receive signals from sensors (four are shown: 124-127) that are coupled to the subject 190. As shown, one of the sensors 124 may be coupled to the subject's arm (e.g., finger), one of the sensors 125 may be coupled to the subject's leg (e.g., toe), one of the sensors 126 may be coupled to the subject's head (e.g., ear), and one of the sensors 127 may be coupled to the subject's other arm (e.g., finger). The signals may include the time to arrival of the pulse wave, time to arrival of dicrotic notch and ejection times at different locations in the body and at different positions (e.g., standing, sitting, lying flat) for a single heartbeat.

The device 100 may also include one or more electronic stethoscope inputs (one is shown: 130). The electronic stethoscope input 130 may be configured to receive a signal from one or more sensors (one is shown: 131) that is coupled to the subject 190. As shown, the sensor 131 may be coupled to the subject's chest.

The device 100 may also include one or more blood pressure inputs (one is shown: 140). The blood pressure input 140 may be configured to receive a signal from one or more sensors (one is shown: 141) that is coupled to the subject 190. The sensor 141 may be or include a blood pressure cuff that is wrapped around the subject's arm. The signal may be or include the subject's blood pressure.

The device 100 may also include a monitor 150 that is configured to display waveforms based upon the signals received. The waveforms may be or include an EKG waveform 152 (e.g., from the EKG input 110), a photoplethysmogram (PPG) waveform 154 (e.g., from the pulse oximeter inputs 120-123), and a phonocardiogram waveform 156 (e.g., from the electronic stethoscope input 130). The monitor 150 may also be configured to display the cardiac output, the stroke volume, the blood pressure, the ejection time, delta ejection time (e.g., the difference in ejection time between different location), delta delta ejection time (e.g., the difference between ejection times between different locations and in different positions), the PAT, the DAT, the systolic and diastolic pulse wave velocity, and the duration from the start of the second heartbeat (S2) to the end of the T wave from the EKG (end T), the electrical and electromechanical restitution curves (e.g., the duration of QT or QS2 interval as function of preceding TQ or S2Q intervals).

Figure 2:
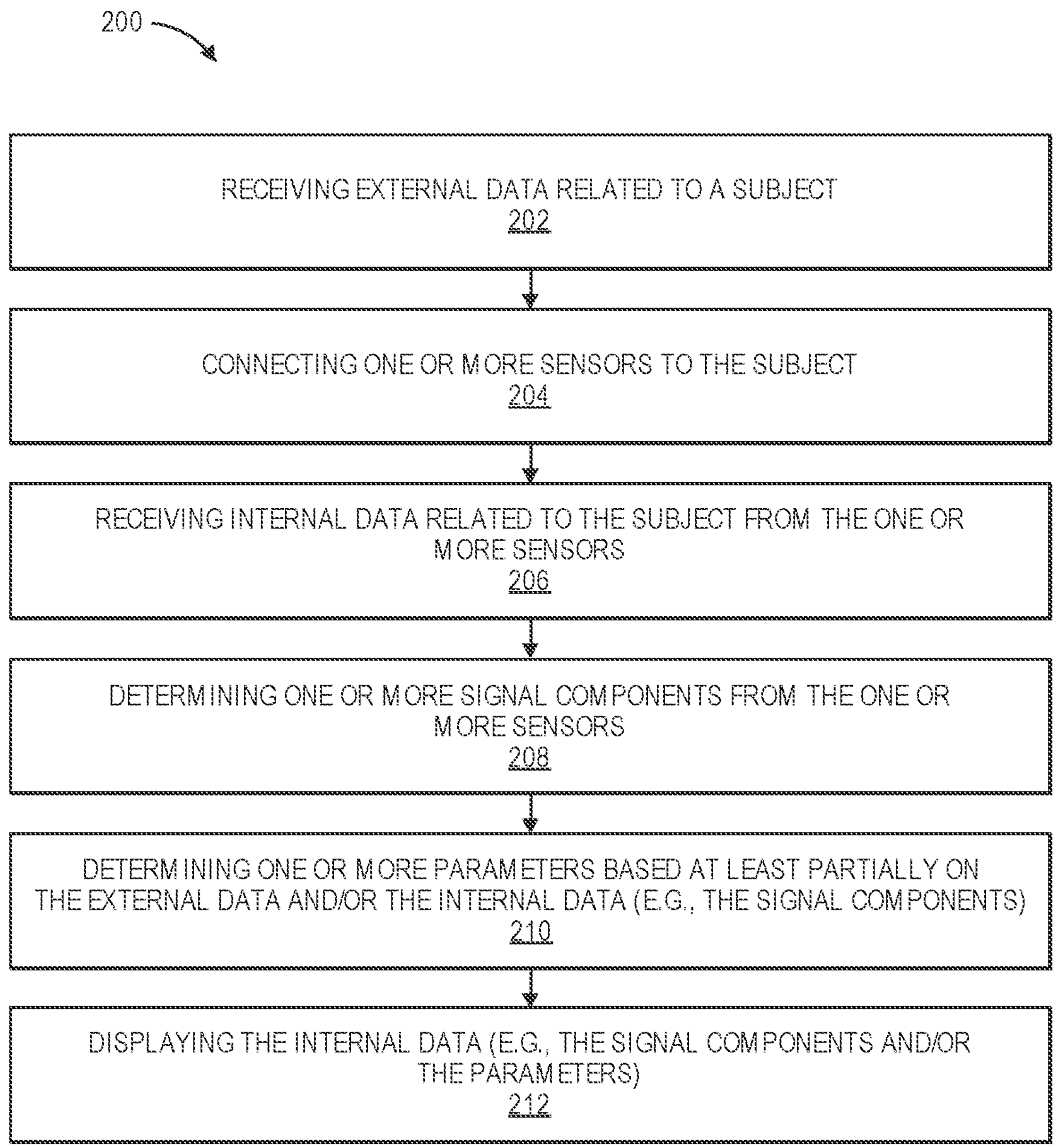
FIG. 2. illustrates a flowchart of a method for measuring an arterial vascular performance of a subject.

FIG. 2. illustrates a flowchart of a method 200 for measuring an arterial vascular performance of a subject 190. The method 200 may include measuring/receiving external data related to the subject 190, as at 202. The external data may be or include anthropometric data. For example, the external data may be or include height, weight, demi-span, and/or the distance from the sternal notch to the index finger, ear lobe, and/or toe.

The method 200 may also include connecting one or more sensors 111-115, 124-127, 131, 141 to the subject 190, as at 204. The sensors may be or include the one or more EKG sensors 111-115 to the chest, shoulders, torso, and/or back, the one or more photoplethysmogram sensors 124-127 to the ears, fingers, and/or toes, the one or more electronic stethoscope sensors 131 to the chest wall in the second intercostal space on the right side or the 3$^{rd}$ intercostal space on the left side along the sternal border, and the blood pressure sensor (e.g., cuff) 141 around the arm. The sensors 111-115, 124-127, 131, 141 may be non-invasive.

The method 200 may also include receiving internal data measured by the sensors 111-115, 124-127, 131, 141, as at 206. The internal data may be received in real-time. The internal data may be high temporal resolution (e.g., 1000-5000 measurements per second).

The method 200 may also include determining one or more signal components from the internal data, as at 208. The signal components from the EKG input 110 may be or include the origin and the peak and end of the P, Q, R, S, T, and U waves. The signal components from the photoplethysmogram inputs 121-123 may be or include the origin, the peak of the arrival wave, the dicrotic notch nadir and post dicrotic notch peak. The signal components from the stethoscope input 131 may be or include the phonocardiogram start of S1 and S2 heart sounds, the peak, and the end as well as pathological heart sounds (S3, S4) or heart murmurs from diseased heart valves.

The method 200 may also include determining one or more parameters based at least partially on the external data and/or the internal data (e.g., the signal components), as at 210. The parameters may be or include the heart rate, the blood pressure, the finger-toe PWV, the ear-toe PWV, and the ejection time at different locations and in different positions. The parameters may also include arterial tree volume (e.g., based on the external data), the stroke volume (e.g., based on the PWV), the cardiac output (which equals the stroke volume×heart rate), the difference in ejection time between different locations derived from the photoplethysmogram waveform 154, and the difference in time delay between the start of the second heart sound and the end of the T wave on the EKG.

The method 200 may also include displaying the internal data, as at 212. This may include displaying the waveforms 152, 154, 156. In other embodiments, this may include displaying the signal components from the internal data. In yet other embodiments, this may include displaying the parameters.

An embodiment in accordance with the present invention provides analysis of a disturbed pattern of a pulse wave front. The analysis results in a non-invasive, real-time diagnostic tool of arterial vascular performance on both a global and regional scale. A novel, non-invasive, real-time monitoring device provides a single number describing how well the arterial tree as a whole is coupled to receive and distribute a stroke volume of a single heartbeat. Changing heart rate, contractility, volume status, afterload, and position of the patient will change the stroke volume, ejection time, and stroke volume distribution. Different vasculatures with different properties (e.g., size and intrinsic stiffness) may be best matched for different stroke volumes and ejection times to provide optimal coupling. The device will allow finding the optimal set of parameters for an individual patient.

The heart uses the arterial tree as a vehicle to deliver the stroke volume and energy associated with a single heartbeat to the microcirculation of peripheral tissues. In a healthy individual, the mean pressure decreases by only 1 to 2 mm Hg between the ascending aorta and a peripheral artery, indicating excellent ventricular arterial coupling with minimal energy loss in the arterial tree itself. To achieve such optimal coupling, the front of the pulse wave should arrive to the microcirculation of different tissues relatively simultaneously. If, in some portions of the vascular tree, pulse waveforms arrive sooner, microcirculation of these tissues may be exposed to pressure overload (e.g., brain and kidney in hypertension). In regions where the pulse waveforms arrive later, or do not arrive at all (e.g., post bypass vasoplegia with low stroke volume), the microcirculation will be under-perfused. To quantify the ventricular-vascular coupling time of the pulse wave front arrival to different peripheral sites of vasculature under different hemodynamic loads are to be measured. The present invention uses different noninvasive techniques of pulse arrival detection, such as pulse oxymetry, tonometry, bio-impedance coupled to an EKG, or other methods of detecting heart cycles, such asphonocardiogram, to measure the arrival of different portions of the pulse wave (e.g., front or dicrotic notch). The time difference between the soonest and slowest pulse wave arrival may be an indicator of coupling (e.g., small differences in the standing position may indicate good coupling and large differences indicating poor coupling. Similarly, small differences in the supine position may indicate poor coupling and large differences indicating good coupling). The time difference between the pulse arrival to a specific vascular bed and remaining heart contraction (=remaining ejection time) may be an indicator of vascular bed hyperperfusion and pressure overload. Similarly, if the ejection time is short, or the PWV is slow, the pulse may not arrive at the most distal vascular bed, leading to hypoperfusion. This may happen when the pulse arrival time is longer than ejection time.

Ejection time at the level of the heart can be estimated by QT, RT or QS2 intervals with current sensors. As the pulse wave generated by the heart ejection travels across the vasculature, it gets distorted. As a result, the ejection time measured at the peripheral site is different than at the central site. Compliant vasculature dampens stroke volume more and, as a result, prolongs the peripherally-measured ejection time. Stiff vasculature does not prolong the ejection time. The stiffness of the vasculature depends on its intrinsic properties but also on distention pressure. Hence, in the standing position, the distention pressure is higher in the lower extremities vasculature and lower in the head vasculature. At the arm, it undergoes minimal changes. The ejection time duration does not vary greatly in patients with intrinsically stiff vasculature that change position from the supine position to the standing position. However, patients with intrinsically compliant vasculature lying flat greatly prolong the ejection time compared to the standing position. This change in ejection time duration with changing positions is a novel non-invasive marker of vascular health. To account for the changes in central ejection time, measuring the delta-delta ejection time is proposed (e.g., the difference between ejection time between two peripheral locations e.g., figure and toe in supine vs standing positions).

The pulse wave velocity and ejection time may be measured simultaneously. The pulse wave length (PWL) may be calculated using the pulse wave velocity and ejection time (e.g., PWV in meters/second*ET in seconds). The pulse wave length is basically the distance the pulse travels in the vasculature during a single heartbeat. When the heart ejection is coupled to the vasculature, the stroke volume fills the arterial tree without over-distention or under-distention. This is achieved when the PWL is coupled to the patient height/distance from the heart to the peripheral tissue beds. In cases when the vasculature is stiff or blood pressure is high, the PWV is high. If the heart rate is slow (e.g., due to beta blockers), the ejection time is long. As a result, the PWL may greatly exceed the patient height/vascular path length, meaning the stroke volume exceeds the capacity of vasculature to accommodate it. This means that the vasculature would be exposed to extra pressure and volume, and the heart would be exposed to extra resistance from overly distended vasculature (e.g., poor coupling). If the PWV is low (e.g., due to low blood pressure), and the ejection time is low (e.g., hypovolemia and high heart rate), then the PWL may be less than the patient height/vasculature length, and poor coupling will occur, meaning the stroke volume is significantly less than the capacity of vasculature to accommodate it. Optimal hemodynamics (e.g., BP, HR, vascular tone) may result in such combinations of PWV and ejection time that the PWL is close to the patient height/distance to measurement site.

The architecture of a normal arterial tree is elegant for its conduit and cushioning functions. The arterial tree receives blood in pulses of stroke volume from the heart. Each pulse is then spread across the arterial tree in a centrifugal manner from the heart to microcirculation in peripheral tissues. It is in the best interest of the organism to deliver blood to the tissues with minimal energy expenditure and time delay. The actual blood flow in the arterial tree is not constant but rather pulsatile, despite the cushioning effect mediated by the elastic nature of the vasculature. Most of blood flow happens at the front of pulse wave during systole. The pulse travels along the arterial tree with a specific speed: the pulse wave velocity. Experimental evidence suggests that this speed is constantly changing in different portions of the vascular tree even in healthy subjects. It is believed that it is due to strong dependence of the pulse wave velocity on the size of the artery and wall tension, the smaller the artery, the higher the pulse wave velocity. As a result, the pulse wave accelerates as it spreads from the heart to the periphery. It is counter-intuitive, but the best analogy is the recently discovered accelerating expansion of the universe. Astrophysicists have known for a long time that the universe is expanding, but they believed that the expansion was slowing down. It is, however, now established that the expansion is indeed accelerating. Similarly, the blood ejected by the heart engages the arterial tree with the accelerating pulse wave velocity as it reaches peripheral tissues even as the average velocity of blood flow in microcirculation is slowing and becomes virtually non-pulsatile. The front of the pulse wave spread may have a unique shape/pattern in a 3D structure of the vascular tree depending on regional PWVs. In healthy vasculature nicely coupled to the heart, the front of the pulse wave arrives to the microcirculation of different tissues relatively at the same time in standing position, ensuring that pressure gradients between areas where the pulse has already arrived (high systolic pressure) and areas with delayed arrival of pulse (low diastolic pressure) are minimal. This ensures the most efficient vascular function of blood and energy transfer. Changing position may change distending pressure within the artery and, as such, its wall tension. Because pulse wave velocity depends not only on arterial size but also on wall tension, changes in position may lead to changes in the shape of the pulse wave front unless compensated for by changes in vascular size due to vascular reactivity. Exercise will increase both stroke volume and blood pressure, and, as such, it will increase the arterial wall tension. Since pulse wave velocity depends not only on arterial size but also on wall tension, hemodynamic changes (e.g., elevation in blood pressure) elicited by exercise may lead to changes in the shape of the pulse wave front and, hence, lead to different time arrival of pulses to different peripheral tissues.

The heart does not work independently, but rather is coupled in a closely orchestrated manner with the vasculature. The properties of the arterial vascular tree exert an enormous effect on the heart function. In addition, a properly functioning vasculature delivers blood and energy from the heart to peripheral tissues in a most efficient way, without imposing extra resistance and energy loss. Investigating ventricular-vascular coupling requires invasive and highly sophisticated technology (e.g., PV loops), which are rarely done in the clinical setting. To quantify vascular health, central pulse wave velocity measurements have been used. These measurements are neither real-time nor continuous, as they are difficult to perform and time-consuming. The proposed device may expand the current understanding of vascular function and bring a new layer of knowledge to the fundamentals of blood transfer from the heart to the peripheral tissues. The proposed method and device hold significant potential for the development of non-invasive, real-time technology to assess global arterial vascular function by assessing the pattern of pulse wave fronts from each heartbeat and how it changes with changes in position, which provides different hydrostatic pressure loads to different portions of the vascular tree. Since measurements are based on routine non-invasive clinical tools (e.g., pulse oximetry and EKG), the device and method can be easily incorporated into clinical settings including operating rooms and critical care units—sites in which optimizing ventricular-vascular coupling might be crucial. The described technology may be easily applied to a cardiovascular patient population. Many patients are elderly with non-compliant stiff vasculature and/or impaired ventricular-arterial coupling. Pulse wave velocity is greatly increased in such patients with stiff central vasculature, and that will have a dramatic impact on the pulse wave front. The smaller the effect that orthostatic changes exert on the pulse wave front, the more intrinsic vascular stiffness is present from elevated blood pressure or arteriosclerosis. In such patients, the pulse wave front may arrive sooner to the proximal organs such as the brain and kidney compared to the arms and legs and will result in a pressure overload of the brain or kidney microcirculation. This can be measured by the difference from the pulse arrival to the head and remaining central ejection time (e.g., start of S2 or end of T). If the stroke volume is low and ejection time is short, then the pulse wave front might not arrive in the distal portions of the body (e.g., fingers and toes) at all, making those tissues hypo-perfused. In patients with peripheral vascular disease, significant obstruction of a particular artery will cause delay in the pressure wave front arrival downstream of an obstruction due to loss of distending pressure.

As such, analysis of the disturbed pattern of the pulse wave front may provide a non-invasive, real-time diagnostic tool of arterial vascular performance on both a global and regional scale. A non-invasive, real-time monitoring device providing a single number of how well the arterial tree as a whole is coupled to receive and distribute a stroke volume of a single heartbeat is also provided with the present invention. Changing heart rate, contractility, volume status, and afterload may change stroke volume and ejection time. Different vasculatures with different properties (e.g., size and intrinsic stiffness) may be best matched for different stroke volumes and ejection times to provide optimal coupling. The device will allow finding the optimal set of parameters for an individual patient. In addition, it can provide an optimal set of parameters for end organ perfusion (e.g., head) in individual patients.

Figure 3:
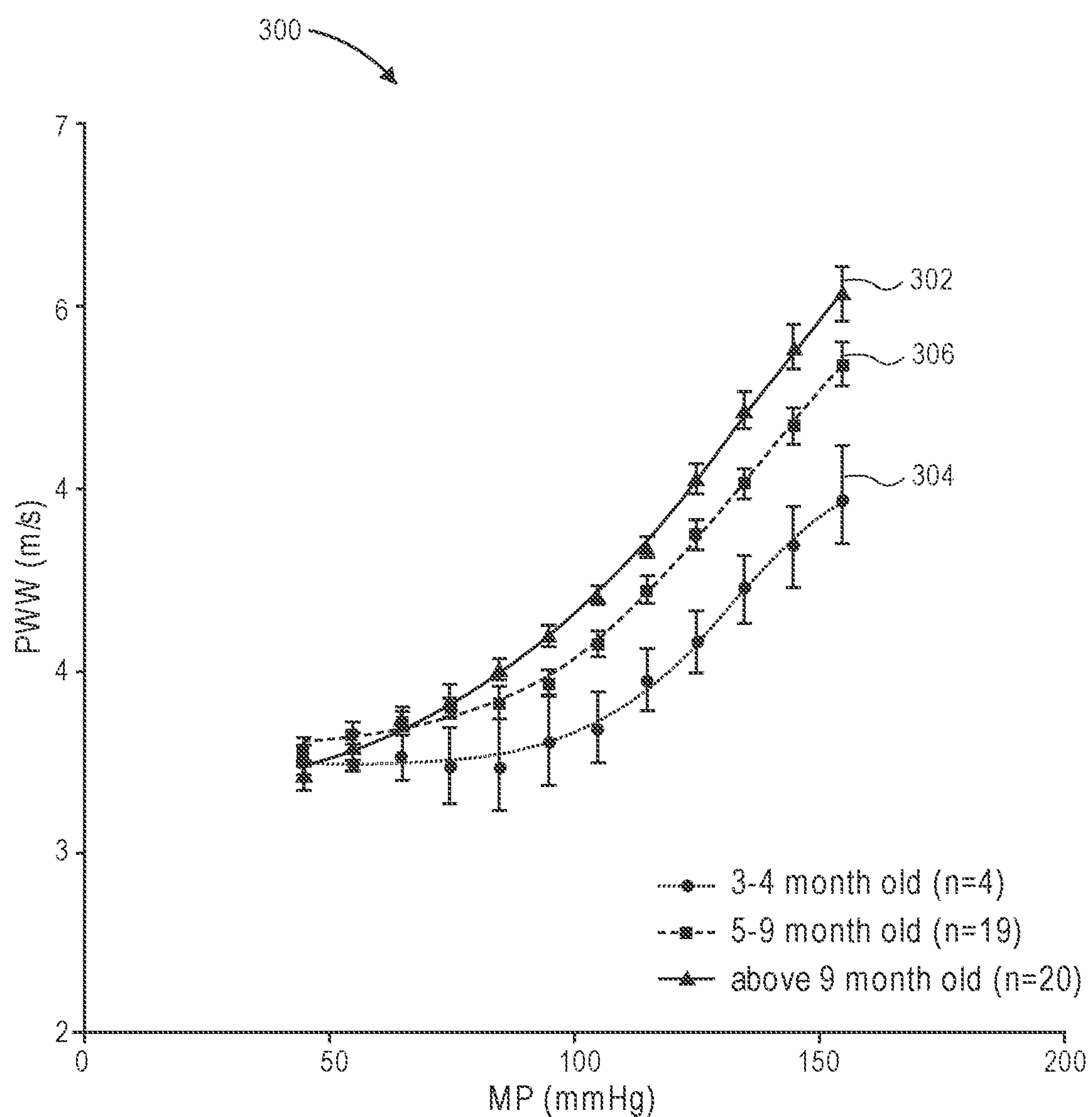
FIG. 3 illustrates a graphical view that shows that a central aortic PWV is not constant, and it is dependent both on blood pressure as well as age of vasculature.

The pulse wave front spreads according to PWV. FIG. 3 illustrates a graph 300 showing that central aortic PWV is not constant, and it is dependent both on blood pressure as well as age of vasculature. Line 302 is an old vasculature, line 304 is a young vasculature, and line 306 is a middle-aged vasculature. As such, for a particular patient with a particular hemodynamic state, the PWV and resultant pulse wave front may be different.

To assess this, an exemplary implementation of the present invention will measure the time to arrival of the pulse wave at different locations in the body for a single heartbeat. To achieve this, several pulse detection probes (e.g., adult pulse oximeter probes) may be simultaneously used and placed at different peripheral parts of body (e.g., fingers of left and right arms, fingers of left and right legs, ears, nose, or lip). The analog pulse detection signals may be digitized to determine the precise time measurements of pulse arrival between different sites for the same heartbeat. The pulse travel time may be precisely timed against the EKG signal (e.g., R wave). To assess the vascular performance in different positions, measurements will be performed while subjects are supine, sitting, standing, or in the head-down position. To assess the vascular performance during exercise or stress testing, measurements will be performed before and after mild-moderate exercise (e.g., 30 knee-bends) or during standardized cardiovascular stress testing. The arrival times may be measured and recorded in real-time electronically. The time delay between the fastest and slowest to arrive, adjusted for heartrate, is a measure of the efficiency of coupling. The time difference in the pulse wave front arrival between the earliest and latest to arrive will provide the index of coupling. The time difference between pulse arrival to specific vascular bed and remaining heart contraction (=remaining ejection time) will be indicator of the particular vascular bed hyperperfusion and pressure overload. Similarly, if ejection time is short or PWV is slow, the pulse might never arrive to the most distal vascular bed, leading to hypoperfusion. This may happen when the pulse arrival time is longer than the ejection time.

In healthy individuals that are free from vascular disease (representing normal physiological conditions), the pulse wave arrives relatively simultaneous to all peripheral tissues despite dramatic changes in path length. Non-simultaneous pulse arrival may lead to the development of pressure gradients between different portions of the arterial tree. Because the arterial tree does not have valves, it may theoretically lead to a "steal phenomenon," where blood from arterial beds with higher pressure (e.g., systolic) flows to another arterial bed with a lower pressure (e.g., diastolic) down a pressure gradient. To put this into perspective, the relative distance from the heart to the ear is 3.3 times shorter than that from the heart to the finger, and 5.7 times shorter compared to the toe, as shown in Table 1 below. If pulse wave velocity is constant across different paths, then one could expect the pulse arrival will be around 3.3 times longer to the finger and 5.7 times longer to the toe, compared to the ear.

TABLE 1

| Cohort demographics and baseline characteristics | | | | | | | | | |
|---|---|---|---|---|---|---|---|---|---|
| | Weight | Height | Length Ratio | | | Systolic BP | Diastolic BP | Age | |
| Subject | (kg) | (kg) | Toe:Ear | Toe:Finger | Finger:Ear | (mmHg) | (mmHg) | (years) | Gender |
| 1 | 80.5 | 188.0 | 5.9 | 1.8 | 3.4 | 113 | 64 | 23 | M |
| 2 | 57.5 | 162.6 | 5.6 | 1.7 | 3.4 | 108 | 68 | 36 | F |
| 3 | 63 | 174.0 | 6.0 | 1.9 | 3.2 | 110 | 63 | 26 | F |
| 4 | 95.5 | 177.0 | 5.8 | 1.8 | 3.3 | 142 | 84 | 39 | M |
| 5 | 54.2 | 164.0 | 5.5 | 1.7 | 3.2 | 111 | 67 | 36 | F |
| 6 | 79.5 | 175.3 | 5.7 | 1.7 | 3.4 | 116 | 62 | 31 | M |
| 7 | 82.1 | 174.0 | 5.7 | 1.7 | 3.3 | 113 | 64 | 41 | M |
| 8 | 47.7 | 165.0 | 5.5 | 1.7 | 3.3 | 98 | 61 | 23 | F |
| 9 | 60.1 | 171.0 | 5.6 | 1.7 | 3.3 | 95 | 58 | 23 | F |
| 10 | 69.5 | 172.7 | 5.7 | 1.7 | 3.3 | 117 | 69 | 29 | M |
| 11 | 94.6 | 177.8 | 5.8 | 1.7 | 3.4 | 128 | 68 | 26 | M |
| Mean | 71.3 | 172.8 | 5.7 | 1.7 | 3.3 | 114 | 66 | 30.3 | |

Exercise and postural change affect pulse wave velocity through the vasodilation of arterioles supplying active muscles and increased vasoconstriction due to sympathetic stimulation. Hence, these factors may also significantly affect pulse arrival times at different peripheral vascular beds. Similar to basal conditions, pulse arrival time to different peripheral vascular beds may be relatively simultaneous after exercise and with postural changes.

Analysis of a disturbed pattern of the pulse wave front may provide a non-invasive, real-time diagnostic tool of arterial vascular performance on both a global and regional scale. A non-invasive, real-time monitoring device may provide a single number describing how well the arterial tree as a whole is coupled to receive and distribute a stroke volume of a single heartbeat. Changing heart rate, contractility, volume status, and afterload may change stroke volume and ejection time. Different vasculatures with different properties (e.g., size and intrinsic stiffness) may be best matched for different stroke volumes and ejection times to provide optimal coupling. The device find the optimal set of parameters for individual patient. The time difference between the pulse arrival to specific vascular bed and remaining heart contraction (=remaining ejection time) may be indicator of vascular bed hyperperfusion and pressure overload. Similarly, if the ejection time is short or PWV is slow, the pulse may not arrive to the most distal vascular bed, leading to hypoperfusion. This may happen when the pulse arrival time is longer than ejection time.

13 healthy volunteers, with no history of vascular or cardiac disease, age 23-41 years old, participated in the study. Inclusion criteria were: Healthy adults of ages 21-50 years, both genders. Exclusion criteria were: Subject refusal to participate, known cardiovascular disease, ages <21 or >50 years, pregnancy, and any disability preventing mild physical exertion. Two subjects who joined the study were excluded. The first was excluded due to inability to finish the study protocol. The second was excluded due to being unable to produce a readable plethysmograph signal on her toes. After verifying that the remaining subjects had no restrictions to participate in the study, each subject's weight, half wingspan (i.e., the distance from the sternal notch to the index finger with the arm in 90 degree lateral extension), and self-reported height were recorded.

A standard 3 lead EKG was placed on the subjects for the continuous monitoring of electrical cardiac activity. First, capillary plethysmograph sensors were placed on both left and right sides for each of the following locations: ear lobes in a standing position, index fingers in a sitting position with hands hanging free by their sides, and on the big toes lying in a supine position. EKG and plethysmograph were simultaneously recorded bilaterally for each location (i.e., ears, index finger, big toe). Then, 3 lead EKG signals were recorded along with plethysmographs from one unilateral ear, finger, and big toe for 30 seconds in the standing, sitting, and supine positions. The EKG and plethysmograph sensors were then removed from the subjects, and a blood pressure cuff was then applied to the subjects to record blood pressure in the standing, sitting, and prone positions, respectively. For the exercise part of the experiment, subjects were then required to perform 30 squats. EKG and plethysmograph sensors were then reattached to subjects' unilateral ear lobe, index finger, and big toe, and recording was redone in the standing, sitting, and supine positions as described above. All data for the 'post exercise' portion was collected within 3 minutes of the subject completing 30 squats. A Powerlab analog to digital converter and Labchart 8.0 software developed by Ad Instruments Ltd, Australia were used to convert and digitally record the EKG and plethysmograph signals.

From the data collected, the pulse arrival time (PAT) to each location (e.g., ear lobe, index finger, and big toe) was assessed by calculating the time delay between 2 characteristic spots: (1) the peak of the R wave on the EKG and (2) the first subsequent positive inflection on the plethysmograph trace. To compare pulse wave arrival times to different tissue beds from the same heartbeat, the corresponding R wave was taken on the EKG as a starting point where time was assigned to be zero.

Figure 4:
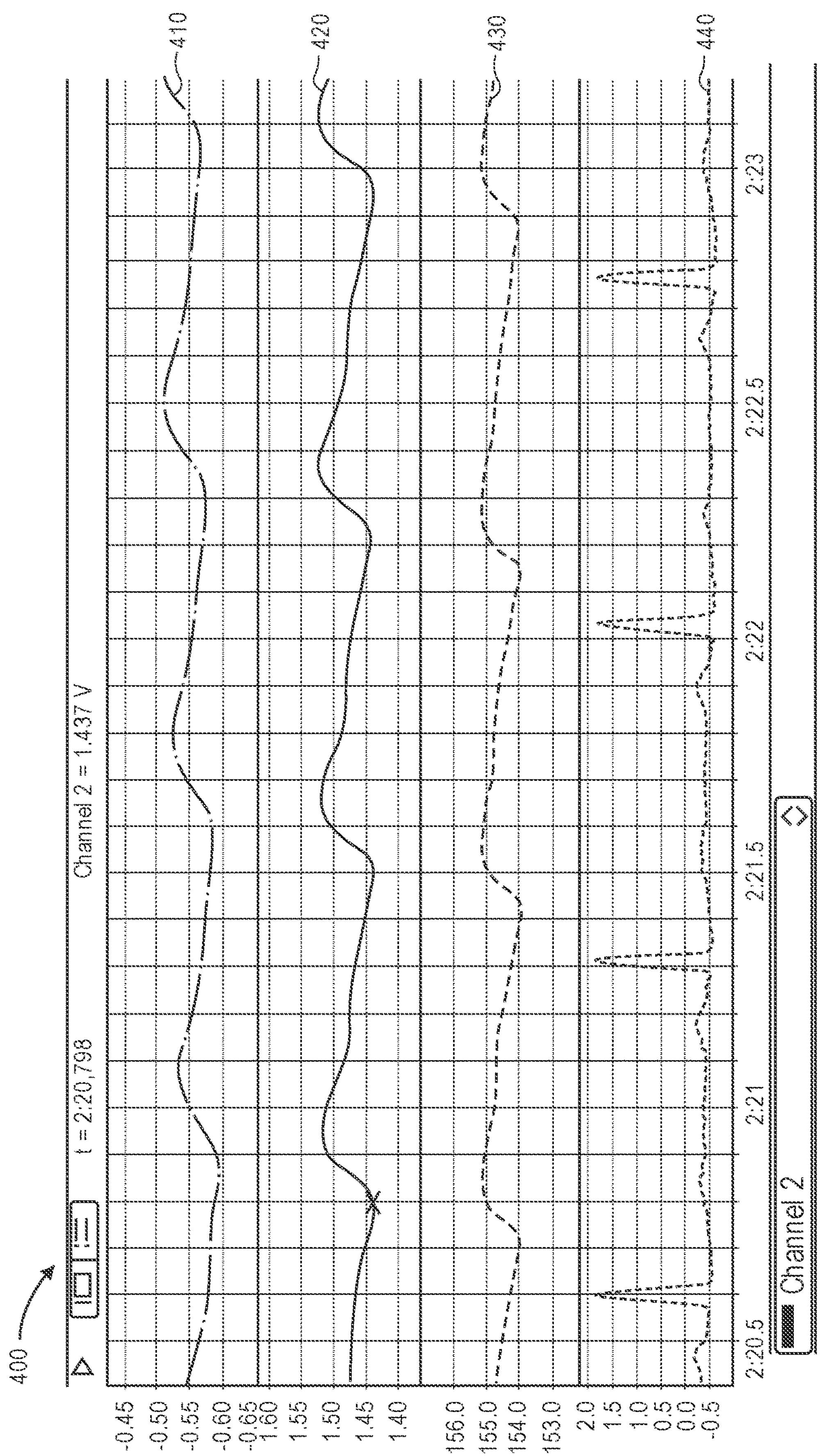
FIG. 4 illustrates a graphical view that shows an example of data presented in Labchart. Periods consisting of 10 consecutive heart beats from different positions (e.g., standing, sitting, supine) before and after exercise were then used to calculated the mean pulse arrival time (PAT), diastolic arrival time (DAT) and ejection time (ET) for the 3 locations: one for the head (e.g., ear lobe), one for the upper extremity (e.g., index finger), and one for the lower extremity (e.g., big toe). Usually PAT are equal between the left side and the right side (e.g., left and right arm); however, more than 3 sensors can placed to increase accuracy (e.g., one on each side).

FIG. 4 shows graphs of three plethysmogram waveforms: the toe 410, the finger 420, and the ear 430, and a graph 440 of the ECG output. Periods consisting of 10 consecutive heart beats from each position (e.g., standing, sitting, supine) before and after exercise were then used to calculated the mean PAT for the 3 locations (e.g., ear lobe, index finger, big toe). To compare the relative time difference between the PAT to ear, finger, and toe, the ratio between the PAT was compared to corresponding locations. The collected data was then tabulated and used for statistical analysis.

Data was analyzed using STATA 12 software (StataCorp, College Station, Tex.). PATs are reported as mean+/−standard deviation. A paired t test was used to compare PAT between different locations before and after exercise as well as PAT ratios between different locations. The threshold for statistical significance was chosen to be $P<0.05$.

Demographics and baseline characteristics of volunteers are presented in Table 1. The average age was 30 years old and ranged from 23 to 41 years old. Females made up 45% of the cohort, and males were 55%. Mean systolic blood pressure was 114 mmHg, and mean diastolic blood pressure was 66 mHg at rest. The average length ratio for toe/ear was 5.7, finger/ear 3.3, toe/finger 1.7. Pulse arrival times from the peak of R wave on the EKG to arrival of the pulse wave are presented for each individual in supplement (1) at rest and (2) post exercise.

These times allowed us to assess the order in which the pulses arrived to different locations. In all subjects, at all positions both at rest and post exercise, the pulse arrival times from shortest to longest were as follows: ear lobe, index finger, and big toe, as shown in Tables 2 and 3, as expected from path length being shortest for the ear lobe and longest for the toe.

PATs to each location (e.g., ears, toes, fingers) were equal for the left and right side. As such, only one side (e.g., either left or right) was compared to measure the PATs at different locations. Table 2 presents data on the effect of exercise. The post-exercise mean PATs at all 3 locations in all 3 positions were shorter compared to at-rest PAT. However, it was not statistically significant for all positions and locations. Table 3 presents the mean PAT for all three positions at-rest and post-exercise.

TABLE 2

Effect of Exerise on Cohort Mean PAT of All Three Positions

| | At rest | Exercise | P-Value |
|---|---|---|---|
| Standing | | | |
| Ear | 0.15 ± 0.02 | 0.12 ± 0.01 | <0.001 |
| Finger | 0.21 ± 0.02 | 0.19 ± 0.03 | 0.26 |
| Toe | 0.26 ± 0.02 | 0.25 ± 0.02 | 0.27 |
| Sitting | | | |
| Ear | 0.14 ± 0.02 | 0.12 ± 0.01 | 0.03 |
| Finger | 0.20 ± 0.01 | 0.18 ± 0.01 | <0.001 |
| Toe | 0.26 ± 0.02 | 0.25 ± 0.01 | 0.03 |
| Supine | | | |
| Ear | 0.12 ± 0.02 | 0.11 ± 0.01 | 0.37 |
| Finger | 0.20 ± 0.01 | 0.18 ± 0.01 | 0.02 |
| Toe | 0.29 ± 0.02 | 0.29 ± 0.02 | 0.70 |

Effects of position and exercise on pulse arrival at the toe are now described. At rest, the longest time taken for pulse arrival to the toe was in the supine position (0.2911 s+/−0.0225) compared to the standing (0.2643 s+/−0.0181, p=0.006) and sitting positions (0.2634 s+/−0.0193, p=0.006). Similarly, during exercise, the longest PAT was seen in the supine position (0.2872 s+/−0.0232) compared to the standing (0.2541 s+/−0.0235, p=0.003) and sitting (0.2472 s+/−0.0137, p<0.001) positions.

Effects of position and exercise on pulse arrival at the index finger are now described. The effect of position on pulse arrival to the index finger was minimal compared to the toe or ear lobe. At rest, the longest time for pulse arrival to the index finger was in the standing position (0.2063 s+/−0.0154) compared to the sitting (0.1987 s+/−0.0112, p=0.12) and supine positions (0.1975 s+/−0.0096, p=0.79). A shorter PAT was seen after exercise, although, similar to rest conditions, the longest PAT occurred in the standing position (0.1940 s+/−0.0316) compared to the sitting (0.1799 s+/−0.1118, p=0.32) and supine (0.1833 s+/−0.0146, p=0.54) positions.

Effects of position and exercise on pulse arrival at the ear are now described. Compared to the toe and finger, the pulse wave always arrived to the ear first at all positions both at rest and post-exercise (see Table 2 and 3). At rest, the longest time for pulse arrival to the ear was in the standing position (0.1452 s+/−0.0162) compared to the sitting (0.1351 s+/−0.0191, p=0.20) and supine positions (0.1182 s+/−0.0158, p<0.001). Similarly, during exercise, the longest PAT was seen in the standing position (0.1213 s+/−0.0115) compared to the sitting (0.1184 s+/−0.0147, p=0.61) and supine (0.1131 s+/−0.0094, p=0.08) p<0.001 positions.

To present relative time delay between corresponding locations, the PAT ratios between toe/ear, toe/finger, and finger/ear were calculated and are presented in Table 4. The PAT ratio differences between locations were much smaller compared to the length ratio difference (finger/ear=3.3 and toe/ear=5.7).

TABLE 3

Effect of Different Positions on Cohort Mean PAT at Rest and Post Exercise

| | At rest analysis (mean PAT ± s.d.) | | | | Post exercise analysis (mean PAT ± s.d.) | | | |
|---|---|---|---|---|---|---|---|---|
| | Mean ear (s) | Mean finger (s) | Mean toe (s) | P-Value | Mean ear (s) | Mean finger (s) | Mean toe (s) | P-Value |
| Standing | 0.13 ± 0.02 | 0.20 ± 0.03 | | <0.001 | 0.12 ± 0.01 | 0.19 ± 0.03 | | <0.001 |
| | 0.13 ± 0.02 | | 0.26 ± 0.02 | <0.001 | 0.12 ± 0.02 | | 0.25 ± 0.02 | <0.001 |
| | | 0.20 ± 0.03 | 0.26 ± 0.02 | <0.001 | | 0.19 ± 0.03 | 0.25 ± 0.02 | <0.001 |
| | Mean ear (s) | Mean finger (s) | Mean toe (s) | P | Mean ear ( s) | Mean finger (s) | Mean toe (s) | P-Value |
| Sitting | 0.13 ± 0.02 | 0.19 ± 0.01 | | <0.001 | 0.12 ± 0.01 | 0.18 ± 0.01 | | <0.001 |
| | 0.13 ± 0.02 | | 0.26 ± 0.02 | <0.001 | 0.12 ± 0.01 | | 0.25 ± 0.01 | <0.001 |
| | | 0.19 ± 0.01 | 0.26 ± 0.02 | <0.001 | | 0.18 ± 0.01 | 0.25 ± 0.01 | <0.001 |
| Supine | 0.12 ± 0.02 | 0.19 ± 0.01 | | <0.001 | 0.11 ± 0.01 | 0.18 ± 0.01 | | <0.001 |
| | 0.12 ± 0.02 | | 0.29 ± 0.02 | <0.001 | 0.11 ± 0.01 | | 0.29 ± 0.02 | <0.001 |
| | | 0.19 ± 0.01 | 0.29 ± 0.02 | <0.001 | | 0.18 ± 0.01 | 0.29 ± 0.02 | <0.001 |

TABLE 4

Summary of Cohort Mean PAT Ratios at Rest and Post Exercise for All Positions

| | PAT ratio | | | | | | | | |
|---|---|---|---|---|---|---|---|---|---|
| | Standing | | | Sitting | | | Supine | | |
| | Toe/Ear | Toe/Finger | Finger/Ear | Toe/Ear | Toe/Finger | Finger/Ear | Toe/Ear | Toe/Finger | Finger/Ear |
| At rest | 1.8202 | 1.2811 | 1.4207 | 1.9496 | 1.3256 | 1.4707 | 2.4627 | 1.4739 | 1.6708 |
| Post Exercise | 2.0948 | 1.3097 | 1.5993 | 2.0878 | 1.3740 | 1.5194 | 2.5393 | 1.5668 | 1.6206 |

The effect of position and exercise on the mean toe/tar PAT ratio, depending on the position and exercise, ranges from 1.84+/−0.20 in the standing position at rest to 2.55+/−0.08 in the supine position post-exercise, which is less than half the mean path length ratio of 5.7. The mean PAT ratio increased, going from standing (1.84+/−0.20) to sitting (1.98+/−0.27) to supine (2.49+/−0.32), meaning that relative to the ear, the PAT at the toe is longest in the supine position and shortest in the standing position. The mean post-exercise ratios for standing, sitting, and supine positions (2.10+/−0.19, 2.11+/−0.20, and 2.55+/−0.08, respectively) were also higher than at-rest ratios (1.84+/−0.20, 1.98+/−0.27, and 2.49+/−0.10, respectively), although not all of these differences were statistically significant.

The effect of position and exercise on the mean toe/finger PAT ratio ranges from 1.28+/−0.10 (standing) to 1.57+/−0.16 (supine), which are smaller values than the expected ratio of 1.7. Changes in position and exercise were not always statistically significant. The mean PAT ratio increased going from standing (1.28+/−0.10) to sitting (1.33+/−0.11) to supine (1.47+/−0.10), but the differences between standing and sitting were not statistically significant both at rest and post-exercise. The mean post-exercise ratios in the standing, sitting, and supine positions (1.32+/−0.13, 1.38+/−0.06, and 1.57+/−0.16, respectively) were higher than the at rest ratios in all positions, but were not statistically significant.

The effect of position and exercise on the mean finger/ear PAT ratio ranges from (1.43+/−0.11) in the standing position at rest to (1.69+/−0.21) in the supine position at rest, which is much shorter than the expected range of 3.3 based on path length ratios. Changes in position and exercise made minimal effect on the ratios. The mean PAT ratio increased going from standing (1.43+/−0.11) to sitting (1.49+/−0.19) to supine (1.69+/−0.21). After exercise, no clear pattern in PAT ratio changes was seen due to positional change: it was shortest at the sitting position (1.53+/−0.15) followed by the standing (1.60+/−0.23) and supine positions (1.63+/−0.15), respectively, but these differences were not statistically significant. Post-exercise PATs were longer compared to at-rest PATs for the standing (1.60+/−0.23 vs. 1.43+/−0.11, p=0.03) and sitting (1.53+/−0.15, p=0.59) positions. The post-exercise PAT was shorter than the at-rest PAT in the supine position (1.63+/−0.15 vs 1.69+/−0.21, p=0.39).

The current study was performed on young, healthy individuals to investigate the physiologic mechanisms of pulse wave distribution across a healthy, compliant arterial tree. Using noninvasive methods, the pattern of pulse wave arrival was measured at three peripheral vascular beds at various positions and exercise statuses in healthy, young volunteers. The arterial tree allows the blood to be transported from the heart to peripheral tissue beds to supply tissue metabolic demands and maintain homeostasis. Blood flow from the heart to the arterial system is provided in a pulsatile manner across the arterial system up to the pre-sphincter arterioles. This pulsatile waveform can be detected at peripheral tissues by devices and techniques such as plethysmography or pulse oximetry. The time taken for the pulse wave to reach the vasculature of various peripheral tissue beds depends on pulse wave velocity in each portion of the vascular tree and path length. The length of a particular vascular pathway remains relatively constant; however, the pulse wave velocity may undergo significant changes in particular arterial segments due to factors such as vascular tone and distending pressure changes. Because the arterial system does not have valves, changes in position such as from lying to standing may cause blood to pool in the lower extremities due to the formation of a hydrostatic gradient from head to toe. In reality, in healthy individuals, the body produces a myogenic response, reacting to this change in hydrostatic pressure by increasing the vascular tone and vasoconstriction in the lower extremities, leading to an increased distending pressure and wall tension in the arteries. This increase in wall tension contributes towards an increased PWV and hence a shorter PAT.

In the present invention, the effect of posture and exercise on pulse wave arrival time to different peripheral tissue beds was studied. The real-time, non-invasive technique of tissue plethysmography was used to detect the pulsatile waveform from which the pulse arrival was deduced. The effect of exercise on pulse arrival time was also explored. A shorter PAT is expected, because exercise causes an increase in the force of contraction, cardiac output, wall tension, and central arterial wall stiffness. Indeed, the findings showed that PAT across all locations were shorter post-exercise.

However, the pulse wave arrived relatively later to the lower extremities compared to fingers and ears as evidenced by the decreasing ratio of toe/ear PAT after exercise as compared to rest. One potential explanation is vasodilation in the metabolically active lower limbs and vasoconstriction in the less metabolically active upper limbs and head as the body optimized metabolic/perfusion matching. As the exercise subjects' performed squats, mainly utilizing muscles in the lower body, metabolic demand in the lower limb muscles would be higher than both the head and upper limbs. The net effect from the vasodilation in the lower limbs and vasoconstriction in the head and upper limbs was an increase in toe/ear PAT ratios seen post-exercise. This is consistent with the fact that an increase in vascular tone (e.g., vasoconstriction) would increase PWV, causing a decrease in PAT and vice versa.

The observations showed that a change in position from horizontal to vertical (e.g., supine to sitting to standing) led to a decrease in PAT to the toe and an increase in PAT to the ear. This might be explained by an increase in hydrostatic pressure in the arteries of lower extremities and a decrease in hydrostatic pressure in the arteries of the head and neck caused by the positional change from horizontal to vertical.

In healthy individuals, the vasculature adapts to the increase in hydrostatic pressure in the lower limbs by increasing wall tension stiffness. Without this response, blood would pool at the lower limbs, and the perfusion of the upper limbs and head would be reduced. Indeed, in many patients with orthostatic hypotension, disorders of the autonomic nervous system prevent this response from occurring, leading to reduced perfusion of the cerebral cortex and syncope.

Studies have shown that an increase in hydrostatic pressure and, hence, increased vascular wall tension, causes an increase in pulse wave velocity. This would explain the findings, where the PAT to the toes was shorter most likely due to the increase in wall tension and, hence, PWV, and the PAT to the ears and fingers was longer due to a decrease in wall tension and PWV when changing from a supine to standing position. However, overall, the PAT changes from lying supine to standing were not drastic, perhaps due to fast adaptation in vascular tone, autonomic nervous system signals, and myogenic responses.

The initial hypothesis was that the pulse wave arrival should be relatively simultaneous to different peripheral tissue beds despite different distances from the heart. It was believed that a grossly unequal time of pulse arrival would lead to a "steal phenomenon" whereby, in some tissue beds, the pulse wave would have already arrived and have systolic blood pressure, while at other tissues beds where the pulse wave had yet to arrive, the pressure would be diastolic, creating a pressure difference within the valve-less arterial system. By altering the vascular tone, it was believed that the body would maintain a relatively simultaneous pulse wave arrival irrespective of postural change or exercise. However, the pulse arrival to the ear, finger, and toe is not the same and is affected to some degree by position and exercise. The time differences presented by the ratios of PAT were relatively small compared to the distance ratios. For example, the distance from the heart to the ear is on average 5.7 times shorter than to the toe, but the toe/ear PAT ratio ranged from 1.8-2.5 depending on position. This supports the initial hypothesis that the body actively tries to maintain the smallest time difference in pulse wave arrivals to peripheral tissue beds irrespective of its distance from the heart. Interestingly, the ratios are smaller for standing and sitting compared to the supine position, meaning that pulse arrival times are more aligned in the vertical position compared to the horizontal position. A more simultaneous pulse arrival throughout the body is more important in the upright positions when people are likely to be more active.

It is shown in the study that the pulse wave reaches the ear before the index finger or big toe. This may be indicative of the body preferentially diverting blood to the cephalic region, although much more exploratory research is needed before coming to this conclusion. It is also unknown whether this pattern of pulse arrival is still true in individuals not included in the demographic studied (e.g., non-healthy, children, or elderly people), and the data collected in this study could be used as a baseline to which future studies could be compared against. The intended sample population was young and healthy adults.

The PowerLabs converter used was unable to distinguish between pressure generated by capillary filling and extremity movements. Subjects had to stay very still while measurements were being taken to ensure a readable trace. The PowerLabs hardware allowed recordation of only 4 tracings at a time, such that signals from both sides of the body could not be recorded simultaneously. Rather, bilateral measurements were first taken to confirm that each pulse arrived simultaneously to both sides at each level (e.g., toe, finger, and ear).

For the exercise portion, it was difficult to standardize the amount of physical activity based on subjects various fitness and strength levels. Indeed, it would be virtually impossible to find a specific exercise that would be equally intense for every subject. Therefore, squats were chosen as an exercise that would be best suited to each individual's body weight and strength level. In the analysis of data, normalization was not done subjects' blood pressure or heart rate, which have been known to confound PWV assessments.

The choice of the R-wave peak on the EKG as the starting point of the PAT measurements also had its limitations, as it included the pre-ejection systolic phase of ventricular contraction, the period between of isovolumetric ventricular contraction before the opening of the aortic valves. In future studies, the usage of cardiac microphone to record the S1 Korotkoff heart sound could be more appropriate in obtaining a PAT sample.

The pulse wave always arrived at the ear first, then to the index finger, and big toe, respectively, regardless of position or exercise status. This could be simply explained by the difference in distances of the three locations from the heart. PATs were shorter post-exercise irrespective of position, most likely due to an exercise-induced increase in sympathetic activity leading to a global increase in pulse wave velocity. When transitioning from a supine to sitting to standing position, the PAT to the ear and finger decreased, while the PAT to the toe increased. This could be explained by an increase in vascular tone in the lower limbs in response to the increase in hydrostatic pressure during the positional change from horizontal to vertical. The PAT ratios between two locations (i.e., toe/ear and finger/ear) were less than half of their respective length difference ratios. The body strives to maintain a relatively simultaneous pulse arrival at different locations despite a large difference in distance.

In the future, the PAT in the aged and diseased populations can also be studied. It is known that aging and cardiovascular diseases significantly affect the pulse wave velocity, and the presenting mechanisms might be distorted in those groups. The current study could serve as the natural comparison group for future investigations in elderly and patients with CV disease.

These steps can be carried out using a non-transitory computer readable medium loaded onto a computing device such as a personal computer, tablet, phablet, smartphone, computer server, or any other computing device known to or conceivable by one of skill in the art. Indeed, any suitable hardware and software known to or conceivable by one of skill in the art could be used. The non-transitory computer readable medium can also be incorporated into the device for assessment of PAT.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A device for measuring an arterial vascular performance of a subject, comprising:

a first input for receiving measurements from an electrocardiogram sensor that is coupled to the subject, wherein the measurements from the electrocardiogram sensor comprise an R wave;

a second input for receiving measurements from a plurality of photoplethysmogram sensors that are coupled to the subject at different locations, wherein the measurements from the photoplethysmogram sensors comprise a first subsequent positive inflection after a peak of the R wave, wherein the device is configured to determine:

pulse arrival times between a time at which an aortic valve of the subject opens to pulse wave arrivals at the different locations, wherein the pulse arrival times are determined by calculating a time delay between the peak of the R wave and the first subsequent positive inflection, and wherein the pulse arrival times to the different locations represent non-invasive markers of the arterial vascular performance of the subject; and ejection times, a delta ejection time, and a delta delta ejection time of the subject based on the measurements from the photoplethysmogram sensors, wherein the delta ejection time represents a difference in the ejection times between the different locations, and wherein the delta delta ejection time represents a difference between the ejection times between the different locations and in different positions.

2. The device of claim 1, wherein the different locations comprise at least two out of a head of the subject, an arm of the subject, and a leg of the subject.

3. The device of claim 1, wherein the different locations comprise a head of the subject, an arm of the subject, and a leg of the subject.

4. The device of claim 1, wherein the different locations comprise an ear of the subject, a finger of the subject, and a toe of the subject.

5. The device of claim 1, wherein the device is configured to determine a metric related to reception and distribution of a pulse stroke volume by an arterial tree of the subject based at least partially upon the pulse wave from the heartbeat pulse arrival times of the subject at the different locations.

6. The device of claim 5, wherein the device outputs a single number to quantify how well the arterial tree receives and distributes the pulse stroke volume.

7. The device of claim 1, wherein the measurements from the photoplethysmogram sensors and the measurements from the electrocardiogram sensor are received and recorded simultaneously.

8. The device of claim 7, further comprising:

a third input for receiving measurements from an electronic stethoscope sensor that is coupled to the subject; and a fourth input for receiving measurements from a blood pressure sensor that is coupled to the subject.

9. The device of claim 5, wherein the device is configured to determine a difference in time between a start of a second heartbeat of the subject and an end of a T wave in the measurements from the electrocardiogram sensor.

10. A method for measuring an arterial vascular performance of a subject, comprising:

receiving measurements from an electrocardiogram sensor that is coupled to the subject, wherein the measurements from the electrocardiogram sensor comprise an R wave;

receiving measurements from a plurality of photoplethysmogram sensors that are coupled to the subject at different locations, wherein the measurements from the photoplethysmogram sensors comprise a first subsequent positive inflection after a peak of the R wave;

determining pulse arrival times between a time at which an aortic valve of the subject opens to pulse wave arrivals at the different locations, wherein the pulse arrival times are determined by calculating a time delay between the peak of the R wave and the first subsequent positive inflection, wherein the pulse arrival times to the different locations represent non-invasive markers of the arterial vascular performance of the subject; and determining ejection times, a delta ejection time, and a delta delta ejection time of the subject based on the measurements from the photoplethysmogram sensors, wherein the delta ejection time represents a difference in the ejection times between the different locations, and wherein the delta delta ejection time represents a difference between the ejection times between the different locations and in different positions.

11. The method of claim 10, wherein the different positions comprise at least two of: a standing position, a sitting position, and a supine position.

12. The method of claim 10, wherein the different locations comprise a head of the subject, an arm of the subject, and a leg of the subject.

13. The method of claim 10, wherein the different locations comprise an ear of the subject, a finger of the subject, and a toe of the subject.

14. The method of claim 13, further comprising:

determining a velocity of the pulse wave between the finger and the toe.

15. The method of claim 14, further comprising determining a metric related to reception and distribution of a pulse stroke volume by an arterial tree of the subject based at least partially upon the pulse wave pulse arrival times from the heartbeat of the subject at the different locations.

16. The method of claim 15, further comprising outputting a single number to quantify how well the arterial tree receives and distributes the pulse stroke volume.

17. The method of claim 14, further comprising determining a difference in time between a start of a second heartbeat of the subject and an end of a T wave in the measurements from the electrocardiogram sensor.

18. The method of claim 14, further comprising:

determining the velocity of the pulse wave based at least partially upon the measurements from the photoplethysmogram sensors, wherein the velocity and the ejection times are determined simultaneously; and determining a length of the pulse wave based at least partially upon the velocity and the ejection time.

19. A device for measuring an arterial vascular performance of a subject, comprising:

an input for receiving measurements from a plurality of photoplethysmogram sensors that are coupled to the subject at different locations, wherein the device is configured to determine ejection times, a delta ejection time, and a delta delta ejection time of the subject based on the measurements from the photoplethysmogram sensors, wherein the delta ejection time represents a difference in the ejection times between the different locations, and wherein the delta delta ejection time represents a difference between the ejection times between the different locations and in different positions.

* * * * *